US00PP20448P2

(12) United States Plant Patent
Deng et al.

(10) Patent No.: US PP20,448 P2
(45) Date of Patent: Nov. 3, 2009

(54) *CALADIUM* PLANT NAMED 'GARDEN WHITE'

(50) Latin Name: ***Caladium* × *hortulanum***
Varietal Denomination: Garden White

(75) Inventors: Zhanao Deng, Wimauma, FL (US); Brent Harbaugh, Wimauma, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/151,720

(22) Filed: May 9, 2008

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

OTHER PUBLICATIONS

Deng Ziaanao et al. Proceedings of the 119th Annual meeting of the Florida State Horticultural Society. Proceedings of the Florida State Horticultural Society 119 p. 409-412. 2006 abstract.*

* cited by examiner

*Primary Examiner*—Annette H Para

(57) ABSTRACT

A distinct cultivar of *Caladium* plant named 'Garden White', characterized by its very large heart shaped leaves, green netted venal pattern, and white interveinal leaf surfaces; demonstrated potential to produce large plants with huge leaves that are larger than other white cultivars when grown in outdoor landscapes.

1 Drawing Sheet

BACKGROUND OF THE INVENTION

'Garden White' was a seedling initially evaluated in 2001 as GC815 originating from the cross-pollination of the *Caladium×hortulanum* cultivar Aaron with the cultivar *Candidum* Junior made in a greenhouse in Bradenton, Fla. 'Aaron', not patented, was selected as the female (seed parent) parent because of its large leaves, vigor, and tuber yield. '*Candidum* Junior', not patented, was the male (pollen) parent selected because of its leaf production, multi-segmented tubers, and bright white interveinal leaf surfaces. Ancestry of 'Aaron' is unknown but '*Candidum* Junior' is believed to be a field mutation of '*Candidum*'. Asexual propagation by tuber division was done in Bradenton, Fla. and Dover, Fla. Evaluation in field and pot studies since 2001 have shown that the unique features of this new *Caladium* plant are stable and reproduced true to type in successive generations of asexual propagation.

SUMMARY OF THE INVENTION

The new *Caladium* has not been observed under all possible environmental conditions. The phenotype may vary somewhat with variations in the environment such as light intensity and temperature, without, however, any variance in genotype.

*Caladiums* are utilized in the ornamental industry as potted plants and landscape plants. They have a diversity of leaf colors that arise from red, pink, and white pigments displayed in solid, spot, and/or blotch patterns in interveinal areas. Veins and leaf margins may be colored or green adding to the diversity of patterns. For plants to be successful in the landscape, they must be vigorous, brightly colored, and have large leaves (unless used for border plants such as is the case for strap or lance leaved cultivars). When forced in containers to be used as an ornamental potted plant, shorter plants with many leaves that emerge quickly are desirable traits. The new *caladium* plant, 'Garden White', has a distinct netted green venation with white interveinal leaf surfaces on very large heart shaped leaves. Leaves have a very narrow green margin and the primary vein is white. It is different in color from 'Aaron', the female parent, which has a wide green margin and the white interveinal pattern is unstable from leaf to leaf, That is, leaves on one plant of 'Aaron' may range in color from only white veins to nearly ¾ the interveinal area of the leaf having a solid white center. It is different in color from '*Candidum* Junior', the male parent, which has green primary veins. It is taller than both parents when planted in the landscape. 'Garden White' has performed well in landscape settings in a number of trials showing the height, leaf size, and vigor necessary for landscape use. Tuber production, a necessary consideration for commercialization of a cultivar by the *caladium* tuber producing industry, has been excellent with tubers produced in the ideal sizes as described in the description section.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description, which accurately describe the colors of the new *Caladium.*

The photograph, labeled FIG. 1, illustrates the overall appearance of the new cultivar, Garden White. The photograph is a side perspective view of a typical plant of 'Garden White' grown in a container.

DETAILED BOTANICAL DESCRIPTION

The following is a detailed description of the new variety with color terminology in accordance with British Color Council and The Royal Horticultural Society, Horticultural Colour Chart, except where general color terns of ordinary dictionary significance are obvious. Wherein dimensions, sizes, and other characteristics are given, it is to be understood that such characteristics are approximations of averages set forth as accurately as practicable. The description herein is from 4 month old specimens grown in Bradenton, Fla, in 2003–2005. Plants used for describing color were grown in 15 cm containers in a 40% shaded greenhouse from Jumbo (6.4 to 8.9 cm diameter) de-eyed tubers.

Botanical classification: *Caladium×hortulanum* cultivar Garden White.

Propagation:

*Type.*—By tuber division.

*Time to develop roots and sprout.*—49 days (Spring—15° C. night to 29° C. day). 25 days (Summer—21° C. night to 35° C. day).

*Root description.*—Dense, thick roots (up to 3 mm at the basal end) with little branching and few lateral roots.

Plant description:

*Plant shape.*—Upright, symmetrical.

*Plant height.*—About 66 cm from top of soil to top of leaf plane 4 months from planting tubers in ground beds in full sun.

*Leaf blade.*—Leaves are peltate, sagitate-cordate, 29–36 cm long and 16–20 cm wide, with green (RHS 157D) palmate-pinnate venation. The upper surface has a green (RHS 137A) margin, lmm wide, bordering the entire leaf except for the basal leaf valley where it is grayed-purple (RHS 185A). Interveinal areas are white (RHS 157C). Netted green (RHS 137D) venation occurs on 75–100% of the leaf surface. The undersurface has a grayed-green (RHS 191A) margin, 1 mm wide. Primary veins are grayed-green (RHS 1157B) and netted venation, grayed-green (RHS 137C), occurs over the entire leaf area. Interveinal areas are quite variable with a green-white (RHS 157C) color near the center to a grayed-green (RHS 194C) near the margin.

*Petiole.*—Petioles are 4–5 mm in diameter and light green (RHS 139D) at the apex, but the colors diffuse into a dark brown (RHS 200A) at the base that is around 8 mm in diameter.

*Tuber.*—Tubers are multi-segmented; a tuber 6.4–8.9 cm in diameter will typically bear 3–4 dominant buds. Tuber surfaces are brown (RHS 200C) with the cortical area yellow-orange (RHS 15C).

*Inflorescence.*—The flowering and reproductive organs do not differ in character from other *caladium* plants.

Performance:

*Garden white.*—Was evaluated for tuber production and plant performance at the Gulf Coast REC—Bradenton, Fla. during 2003 and at Dover, Fla. in 2004. The soil was an EauGallie fine sand with about 1% organic matter and a pH of 6.2. Plants were grown in a plastic-mulched raised-bed system maintaining a constant water table with seep irrigation. The beds were 91 cm wide and 20 cm high with 2.54 cm *caladium* seed pieces planted 15 cm apart in 3 rows (Bradenton) or 2 rows (Dover) also spaced 15 cm apart. Osmocote 18N-2.6P-10K 8–9 month controlled release fertilizer was applied to the bed surface when shoot tips were emerging from the soil with N at 336 $kgXha^{-1}$.

Plots were organized in a randomized complete block design consisting of three replications. For tuber production, each plot was 1.2 $m^2$ and contained 30 propagules. An analysis of variance was conducted in order to compare the performance of >Garden White= to its parents and other important other commercially important white fancy-leaf cultivars. For plant performance in the landscape, three plants were measured in the center of each plot and plant height, leaf number, and leaf size were measured mid-summer. Since year did not significantly influence plant performance, the data was averaged over the 2 years.

The weight of 'Garden White' tubers from each plot exceeded all cultivars except 'June Bride' in 2003 (Table 3). In 2004, tuber weights were similar for 'Garden white', 'Moonlight' and 'White Christmas' and exceeded other cultivars except 'June Bride'. The production index (an economic indicator of crop value) was highest for 'Garden White' and 'June Bride' compared to all other cultivars in 2003. In 2004, the production index for 'Garden White' exceeded other cultivars except 'Moonlight' and 'June Bride' that had similar high values. Although the same number (30) of seed pieces were planted per plot, more than 30 tubers were harvested since several sprouts may emerge per tuber and result in more han one tuber developing per planted seed piece. This of course is advantageous as it can increase profitability. 'Garden White' had more marketable tubers per plot (59) than all other cultivars in 2003, and 45 marketable tubers in 2004 which was similar to 'Moonlight' and 'White Christmas'. The distribution of tubers within grades also is an important factor for marketing. 'Garden White' had a good distribution of tubers with approximately 86% in the No. 1, Jumbo, and mammoth categories. These sizes are ideal for tubers marketed for landscape use.

Landscape performance of cultivars grown under full-sun conditions was evaluated in 2003 and 2004 on the same plots used for evaluating tuber production. Plant height, number of leaves, and foliar characteristics were recorded approximately 4 months after planting. Overall plant performance ratings were excellent for all rating periods (22 July, 31 Aug, and 16 Nov). >Garden White= was the tallest cultivar evaluated in this test, out growing both parents.

>Florida Garden White= tubers were forced in 10-cm containers and its growth was compared to four white-fancy commercial cultivars. No. 1 tubers were planted in a peat/vermiculite mix on Apr. 22, 2005. The study was conducted in a glasshouse with 25% light exclusion during the summer in Bradenton, Fla. Average daily temperatures ranged from a low of 16EC night to 29EC day during the experiment. Plant height, number of leaves, and foliar characteristics were recorded 7 weeks after planting.

>Garden White= sprouted in 25 (intact) or 27 days (de-eyed) and was earlier than all cultivars except '*Candidum*' that had similar sprouting dates of 27 and 30 days (Table 3). Intact plants of 'Garden White' were 37 cm tall, similar in height to 'Aaron' and White Christmas, while plant height was 29 cm for de-eyed plants. All cultivars had similar plant heights when de-eyed. 'Garden White' and 'Aaron' only had 4 leaves on intact plants, but 11 on de-eyed plants. 'Garden White' had the largest leaves of all cultivars tested. The performance of >Garden White= from intact tubers suggested that it is best suited to landscape use. If used in small pots, 'Garden White' would perform best if de-eyed tubers were treated with a growth retardant.

In summary, >Garden White= is intended for use in the landscape or large containers. Its performance was outstanding for a white cultivar, as leaves of most white cultivars deteriorate under full sun conditions. It is very vigorous, tall, and with its large leaves, would be an ideal garden or landscape plant.

TABLE 1

Plant performance approximately 4 months from planting 2.54 cm tuber propagules in ground beds in full sun in 2003 and 2004. Values presented are means of three replications with three plants measured per plot per year, averaged over 2 years.

| | Plant | Leaf | | | Overall | | |
|---|---|---|---|---|---|---|---|
| | height | | length | width | performance rating[2] | | |
| Cultivar | (cm) | number | (cm) | (cm) | Early | Mid | Late |
| Aaron | 53.8 | 16.3 | 28.9 | 17.5 | 3.8 | 4.0 | 3.2 |
| *Candidum* | 46.1 | 13.3 | 28.3 | 18.1 | 3.3 | 3.7 | 3.5 |
| *Candidum* Jr. | 26.1 | 15.9 | 22.1 | 14.4 | 2.8 | 2.5 | 2.7 |
| Garden White | 66.4 | 17.0 | 32.4 | 18.1 | 4.7 | 4.5 | 4.2 |
| June Bride | 50.7 | 13.0 | 30.9 | 19.3 | 3.7 | 4.3 | 3.2 |
| Moonlight | 53.1 | 18.4 | 27.8 | 20.0 | 5.0 | 4.5 | 4.3 |
| White Christmas | 51.1 | 14.6 | 31.4 | 19.8 | 5.0 | 4.3 | 3.3 |
| LSD ($\alpha$ = 0.05) | 8.0 | 3.8 | 3.5 | 1.7 | 0.9 | 0.5 | 1.0 |

[2]Overall plant performance was rated Jul. 22 (early), Aug. 31 (mid), and Nov. 16 (late), 2004.

TABLE 2

Plant performance for *caladium* cultivars grown in 10-cm containers in a 25% shaded glasshouse, 2005, Bradenton Florida. Values represent the means of eight plants produced from intact (I) or de-eyed (D) No. 1 tubers (3.8 to 6.4 cm in diameter) planted individually per container.

| | Sprout (days)[2] | | Plant ht (cm) | | Leaf (no.) | | Leaf length (cm) | | Leaf width (cm) | |
|---|---|---|---|---|---|---|---|---|---|---|
| Cultivar | I | D | I | D | I | D | I | D | I | D |
| Aaron | 34 | 32 | 38 | 29 | 4 | 11 | 27 | 20 | 19 | 15 |
| *Candidum* | 27 | 30 | 30 | 25 | 9 | 10 | 26 | 22 | 17 | 15 |
| Florida Moonlight | 32 | 30 | 28 | 26 | 7 | 8 | 32 | 28 | 22 | 21 |
| Garden White | 25 | 27 | 37 | 29 | 4 | 11 | 33 | 23 | 24 | 15 |
| White Christmas | 38 | 30 | 36 | 27 | 9 | 9 | 29 | 22 | 21 | 15 |
| LSD (a = 0.05) | 2.8 | ns | 5.9 | 3.6 | 2.2 | 2.8 | 2.8 | 3.6 | 2.1 | 2.5 |

[2]Number of days from planting to the first unfurled leaf.

TABLE 3

Tuber weights, production index, and tuber grade distribution of *caladium* cultivars harvested in 2003 and 2004. Values presented are means of three replications with 30 propagules per 1.2-m2 plot per year.

| | Tuber | | |
|---|---|---|---|
| | Weight (g) | P. I.[y] | Marketable (number) |
| | Year 2003 | | |
| Aaron | 2867 | 91 | 29 |
| *Candidum* | 2784 | 98 | 33 |
| *Candidum* Jr. | 3082 | 107 | 37 |
| Garden White | 6338 | 185 | 59 |
| June Bride | 7741 | 161 | 40 |
| White Christmas | 3192 | 123 | 37 |
| LSD ($\alpha$ = 0.05) | 1039 | 31 | 10.2 |
| | Year 2004 | | |
| Aaron | 3255 | 95 | 29 |
| *Candidum* | 2860 | 96 | 35 |
| *Candidum* Jr. | 2431 | 86 | 36 |
| Garden White | 4879 | 153 | 45 |
| June Bride | 6038 | 143 | 37 |
| Moonlight | 4253 | 140 | 45 |
| White Christmas | 4062 | 113 | 39 |
| LSD ($\alpha$ = 0.05) | 885 | 31 | 7.8 |

TABLE 3-continued

Tuber weights, production index, and tuber grade distribution of *caladium* cultivars harvested in 2003 and 2004. Values presented are means of three replications with 30 propagules per 1.2-m2 plot per year.

| | Tuber distribution[2] (%) | | | | |
|---|---|---|---|---|---|
| | Super mam | Mam | Jumbo | No. 1 | No. 2 |
| | | Year 2003 | | | |
| Aaron | 3 | 23 | 24 | 38 | 12 |
| *Candidum* | 1 | 4 | 30 | 43 | 14 |
| *Candidum* Jr. | 3 | 8 | 32 | 38 | 19 |
| Garden White | 0 | 16 | 31 | 40 | 13 |
| June Bride | 8 | 29 | 24 | 24 | 15 |
| White Christmas | 0 | 14 | 49 | 26 | 11 |
| LSD ($\alpha$ = 0.05) | 7.0 | 17.6 | 21.3 | 21.6 | 8.5 |
| | | Year 2004 | | | |
| Aaron | 0 | 15 | 41 | 35 | 9 |
| *Candidum* | 2 | 6 | 26 | 54 | 12 |
| *Candidum* Jr. | 0 | 5 | 21 | 47 | 27 |
| Garden White | 1 | 19 | 39 | 31 | 11 |
| June Bride | 2 | 28 | 40 | 17 | 13 |
| Moonlight | 0 | 15 | 38 | 24 | 24 |
| White Christmas | 0 | 2 | 43 | 52 | 3 |
| LSD ($\alpha$ = 0.05) | 3.2 | 16.4 | 17.0 | 28.3 | 11.3 |

[2]Tubers graded by maximum diameter; No. 2 (1" to 1.5"), No. 1 (1.5" to 2.5"), Mammoth (mam = 2.5" to 2.5"), and Super Mammoth (super mam = > 4.5").

[y]The production index is an indicator of economic value of the crop harvested and is calculated as: N (No. 2s) + 2N (No. 1s) + 4N (Jumbos) + 6N (Mammoth) + 8N (Super Mammoth); where N = number of tubers in each grade.

It is claimed:

1. A new and distinct cultivar of *Caladium* plant named 'Garden White', as illustrated and described.

* * * * *

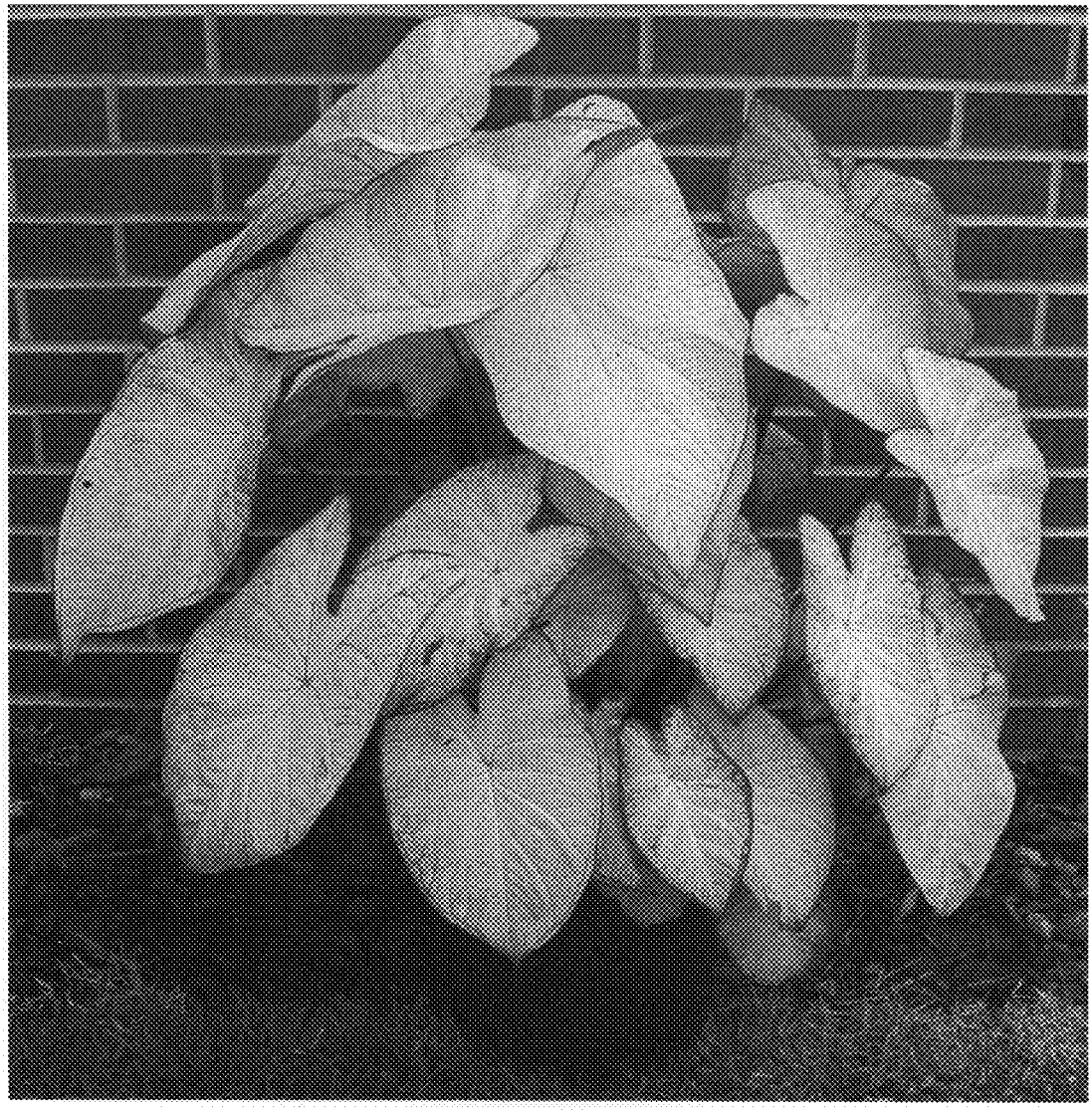
Fig. 1 – Caladium Plant named 'Garden White'